(12) United States Patent
Boahene et al.

(10) Patent No.: US 12,721,728 B2
(45) Date of Patent: Sep. 1, 2026

(54) VACUUM FORMING OF THERMOPLASTIC BIOABSORBABLE SCAFFOLDS FOR USE IN AURICULAR RECONSTRUCTION

(71) Applicant: THE JOHNS HOPKINS UNIVERSITY, Baltimore, MD (US)

(72) Inventors: Kofi Boahene, Baltimore, MD (US); Christopher Razavi, Baltimore, MD (US); Andrew Lee, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1178 days.

(21) Appl. No.: 17/762,419

(22) PCT Filed: Sep. 21, 2020

(86) PCT No.: PCT/US2020/051766
§ 371 (c)(1), (2) Date: Mar. 22, 2022

(87) PCT Pub. No.: WO2021/061559
PCT Pub. Date: Apr. 1, 2021

(65) Prior Publication Data

US 2022/0338993 A1 Oct. 27, 2022

Related U.S. Application Data

(60) Provisional application No. 62/904,218, filed on Sep. 23, 2019.

(51) Int. Cl.

| | |
|---|---|
| ***B29C 51/10*** | (2006.01) |
| ***A61F 2/30*** | (2006.01) |
| ***A61L 27/18*** | (2006.01) |
| ***A61L 27/36*** | (2006.01) |
| ***A61L 27/56*** | (2006.01) |

(Continued)

(52) U.S. Cl.
CPC .......... *A61F 2/30756* (2013.01); *A61L 27/18* (2013.01); *A61L 27/3616* (2013.01); *A61L 27/56* (2013.01); *A61L 27/58* (2013.01); *B29C 51/10* (2013.01); *B33Y 40/20* (2020.01)

(58) Field of Classification Search
CPC ...................................................... B29C 51/10
See application file for complete search history.

(56) References Cited

FOREIGN PATENT DOCUMENTS

| | | | |
|---|---|---|---|
| CA | 2958544 | * | 5/2019 |
| WO | WO98/46164 | * | 10/1998 |
| WO | 2016200201 A1 | | 12/2016 |

(Continued)

OTHER PUBLICATIONS

International Preliminary Report on Patentability in corresponding Application No. PCT/US2020/051766 mailed on Mar. 15, 2022, 5 pages.

(Continued)

*Primary Examiner* — Edmund H Lee

(74) *Attorney, Agent, or Firm* — MH2 Technology Law Group LLP

(57) ABSTRACT

Provided is a polymeric auricular scaffold for use in auricular implants and methods for making them. The disclosed polymeric auricular scaffold is formed using a biocompatible polymer sheet that is vacuumed formed into a shape representing auricular cartilage using a vacuum forming mold.

6 Claims, 6 Drawing Sheets

(51) Int. Cl.
*A61L 27/58* (2006.01)
*B33Y 40/20* (2020.01)

(56) References Cited

FOREIGN PATENT DOCUMENTS

WO WO2016/200201 * 12/2016
WO WO-2018200816 A1 * 11/2018 ........... A61F 2/0059

OTHER PUBLICATIONS

Ilyin (Ru Examiner), International Search Report and Written Opinion in corresponding International Application No. PCT/US2020/051766 mailed on Jan. 28, 2021, 6 pages.

* cited by examiner

VACUUM FORMING OF THERMOPLASTIC BIOABSORBABLE SCAFFOLDS FOR USE IN AURICULAR RECONSTRUCTION

CROSS REFERENCE TO RELATED APPLICATIONS

This application is a national stage entry from International Application No. PCT/US2020/051766, filed on Sep. 21, 2020, published as International Publication No. WO 2021/061559 A1 on Apr. 1, 2021, and claims the benefit of U.S. Provisional Application No. 62/904,218 filed Sep. 23, 2019, the contents of which are incorporated by reference herein in their entireties.

FIELD

The present disclosure generally relates to medical implants and, more particularly, to auricle implants and methods for forming auricle implants using vacuum forming.

BACKGROUND

Microtia is a congenital condition that results in malformation of the auricle and, at times, the external auditory canal. Surgical reconstruction of the auricle generally requires harvesting autologous costal cartilage, for example, from the rib area which may be limited in supply, difficult and time consuming to sculpt, and may result in donor site morbidity including hemopneumothorax. In addition, the guides for rib graft harvest and carving are most commonly a two-dimensional drawing from the contralateral ear. This can make achieving the desired three-dimensional shape of the cartilage challenging, resulting in a lack of symmetry between the intact and reconstructed auricles. Furthermore, even if the costal cartilage has been sculpted appropriately, there can still be unpredictable cosmetic results. Although custom and standardized auricular polymer implants have been used to combat the aforementioned limitations, there are concerns with implant extrusion, surgical site infection, as well as a lack of tactile fidelity to native auricular cartilage.

Use of crushed autologous cartilage grafts is promising alternative. Crushed autologous cartilage, however, lacks the structural integrity to maintain a specific shape. To address this shortcoming, dissolvable biocompatible 3D printed scaffolds, in the desired shape, have been used to provide support to crushed autologous cartilage in an animal model. The goal of such an approach is to reduce the lengthy operative time needed to harvest and carve costal cartilage, reduce donor site morbidity, while also improving the tactile fidelity of the reconstruction. There is also the potential to reduce the risks of surgical site infection and implant extrusion that are present with currently available synthetic porous implants. Currently, these animal models use auricular scaffolds for crushed autologous cartilage that have been 3D printed (also referred to as additively manufactured) using poly(lactic-co-glycolic acid) (PLGA), which is a resorbable biocompatible material. The 3D printed auricular scaffolds are then filled with crushed cartilage and can be implanted in a similar manner to polymer implants. While this process addresses the deficits with tactile fidelity and implant extrusion discussed above, concerns remain in regards to symmetry/cosmesis and cost. Currently available 3D-printers that are capable of printing in PLGA or other similar bioabsorbable materials are limited in their resolution. This leads to cartilage scaffold implants that may not adequately represent anatomic features of the auricular cartilage causing asymmetry and poor cosmesis of the reconstructed auricle.

Improved biocompatible scaffolds that better represent anatomic features of the auricular cartilage and cost-effective methods for making them would be desirable.

SUMMARY

According to the present teachings, a method of forming an auricular scaffold is provided. In the method, a mold comprising a shape representing an auricular cartilage is provided. A biocompatible polymer sheet is then heated to a first temperature and the biocompatible polymer sheet that was heated is contacted to the mold. A vacuum is then applied to the biocompatible polymer sheet that was heated to draw the biocompatible polymer sheet over the mold. The biocompatible polymer sheet that was drawn over the mold is then cooled below the first temperature to fix the shape representing the auricular cartilage in the polymer sheet.

According to the present teachings, the method of forming an auricular scaffold can optionally include providing a mold by creating a data file representing the auricular cartilage of a patient and printing, by additive manufacturing, the mold using the data file. The data file can optionally represent measurements made by CT segmentation or 3D-scanning. The method of forming an auricular scaffold can optionally include printing by additive manufacturing by one or more of stereolithography (SLS), fused deposition modeling (FDM), selective laser sintering (SLS), fused deposition modeling (FDM), digital light processing (DLP), selective laser melting (SLM), laminated object manufacturing (LOM), and electron beam melting (EBM). The method of forming an auricular scaffold can further optionally include the biocompatible polymer sheet comprising one or more of poly(lactic-co-glycolic acid) (PLGA), poly (I-lactic acid) (PLLA), or other biocompatible polymer. The biocompatible polymer sheet can have a thickness of about 0.05 to about 2 mm and/or comprise a plurality of holes. The method of forming an auricular scaffold can further optionally include one or more of removing the biocompatible polymer sheet that was drawn over the mold and cooled from the mold, trimming excess biocompatible polymer sheet to form the auricular scaffold, and packing the auricular scaffold with crushed cartilage to form an auricular graft.

According to the present teachings, a method of reconstructing an external ear using an auricular scaffold is provided. In the method, a mold comprising a shape representing an auricular cartilage is provided and a polymer auricular scaffold is formed by vacuum forming, wherein the polymer auricular scaffold comprises poly(lactic-co-glycolic acid) (PLGA), poly (I-lactic acid) (PLLA), or another biocompatible polymer. Crushed autologous cartilage is then provided and an auricular implant is formed by packing the polymer auricular scaffold with the crushed autologous cartilage. The auricular implant can then be affixed to a patient.

According to the present teachings, the method of reconstructing an external ear using an auricular scaffold can optionally include providing a vacuum formed polymer auricular scaffold by creating a data file representing the auricular cartilage of the patient and printing, in 3D, a mold representing the auricular cartilage of the patient using the data file. The method of reconstructing an external ear using an auricular scaffold can further optionally include one or more of vacuum forming a polymer sheet comprising a plurality of holes over the mold representing the auricular cartilage of the patient and forming an auricular implant by packing the polymer auricular scaffold with the crushed cartilage by mixing one or both of tissue glue and platelet rich plasma with the crushed cartilage.

According to the present teachings, an auricular scaffold structure is provided. In the auricular scaffold structure is a mold representing an auricular cartilage. Also in the auricular scaffold structure is an auricular scaffold disposed on the mold, wherein the auricular scaffold comprises a biocompatible polymer capable of being vacuum formed.

According to the present teachings, the auricular scaffold can optionally include one or more of the vacuum forming mold representing an auricular cartilage formed by additive manufacturing based on a data file and the data file comprises measurements from 3D scanning of an auricular cartilage of a patient. The auricular scaffold can further optionally include one or more of the biocompatible polymer comprising poly(lactic-co-glycolic acid) (PLGA), poly (I-lactic acid) (PLLA), or combinations thereof and the auricular scaffold disposed on the vacuum forming mold comprises a plurality of pores.

According to the present teachings, an auricular scaffold is provided. The auricular scaffold includes a single biocompatible polymer sheet comprising a size and a shape representative of an auricle, wherein the single biocompatible polymer sheet further comprises a plurality of holes that extend through the single polymer sheet and are positioned to facilitate one or more of packing, retention, and structural stability of packed crushed cartilage.

According to the present teachings, the auricular scaffold can optionally include the single biocompatible polymer sheet comprising a size and shape representative of an auricle not comprising texturing. The auricular scaffold can further optionally include comprising a surface roughness Ra of about 10 or less.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate the present disclosure and together with the description, serve to explain the principles of the present disclosure.

DESCRIPTION

Reference will now be made in detail to exemplary implementations of the present disclosure, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary implementations in which the present disclosure may be practiced. These implementations are described in sufficient detail to enable those skilled in the art to practice the present disclosure and it is to be understood that other implementations may be utilized and that changes may be made without departing from the scope of the present disclosure. The following description is, therefore, merely exemplary.

Currently, auricular scaffolds formed by 3D printing (also referred to herein as additive manufacturing) are not cost effective, may not adequately represent anatomic features of the auricular cartilage, and are limited to animal models. The auricular scaffolds disclosed herein are made by vacuum forming which provides the advantages of flexibility, cost effectiveness, and speed of production. Tooling for vacuum forming is also widely available and less expensive than high end 3D printers. As a result, the auricle scaffolds disclosed herein provide superior representation of anatomic features of the auricular cartilage compared to 3D printed auricular scaffolds and are more cost effective.

Figure 1:
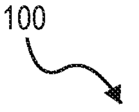
FIG. 1 depicts a method to form polymer auricle scaffolds using vacuum forming in accordance with the present teachings.
Figure 1:
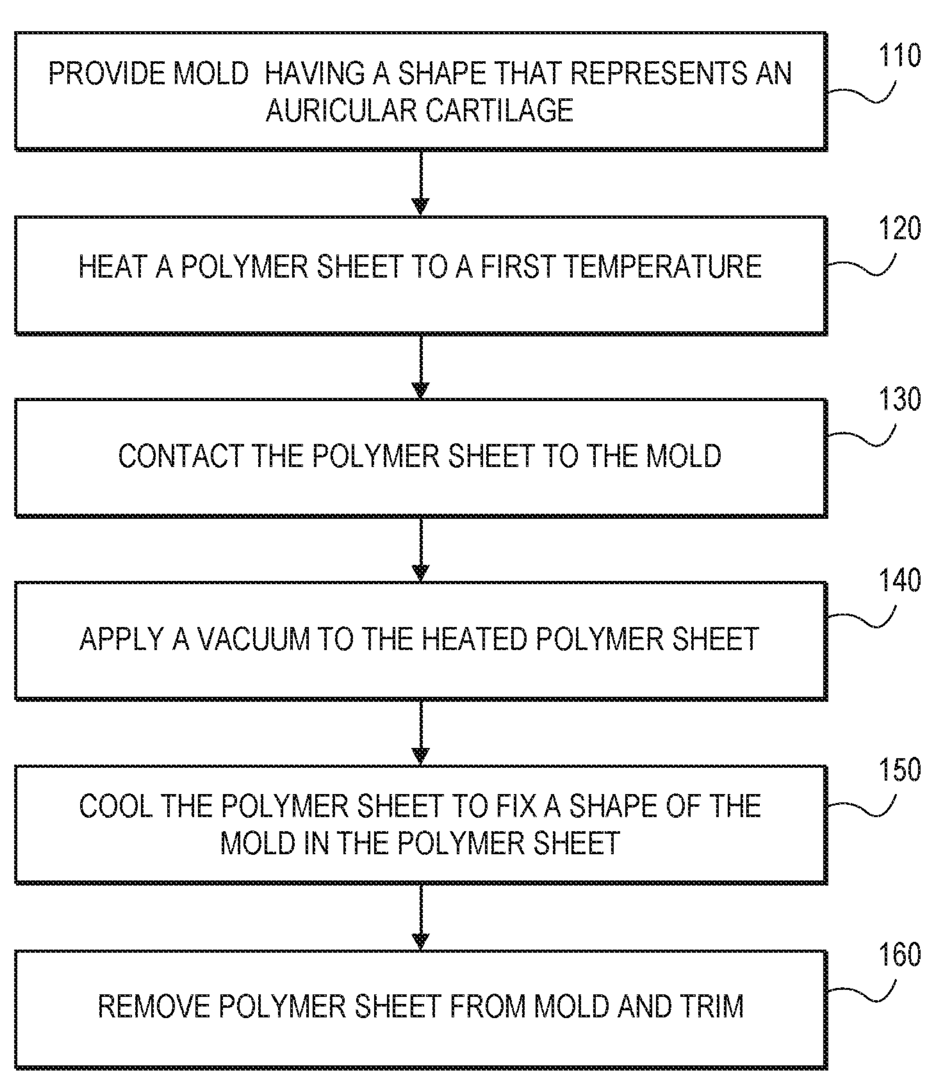

FIG. 1 depicts a method 100 of forming an auricular scaffold according to the present teachings. At 110 of method 100, a mold having a shape that represents an auricular cartilage is provided. The mold can have a size and shape that varies dependent on the patient requiring the auricular graft. For example, standardized shapes and sizes can be used depending on the patient's age, sex, and size. The mold can further include vents to facilitate drawing a vacuum as discussed herein.

Optionally, a customized mold can be provided. The customized mold can be fabricated by measuring the auricular cartilage of a patient's contralateral ear of normal anatomy, for example, using CT segmentation or 3D-scanning. A data file can then be created based on the CT segmentation data or 3D-scanning data. Using the data file, the customized mold can be 3D printed by methods including, but not limited to, stereolithography (SLS), fused deposition modeling (FDM), selective laser sintering (SLS), fused deposition modeling (FDM), digital light processing (DLP), selective laser melting (SLM), laminated object manufacturing (LOM), electron beam melting (EBM), other additive manufacturing methods or combinations thereof.

After providing the mold, a biocompatible (also referred to herein as bioabsorbable) polymer sheet can be heated at 120 of method 100. To facilitate heating and subsequent steps of vacuum forming, the biocompatible polymer sheet can be mounted in a frame. The biocompatible polymer sheet mounted in the frame can be a single biocompatible polymer sheet. The biocompatible polymer sheet can be formed of a thermoplastic polymer. For example, the biocompatible polymer sheet can be formed of a biocompatible polymer, including, but not limited to, poly(lactic-co-glycolic acid) (PLGA) and poly (I-lactic acid) (PLLA) of varying levels of cross-linking and percentages of lactic and glycolic acid. The percentages of lactic acid to glycolic acid can vary, for example, from 85:15 to 75:25. The biocompatible polymer sheet can have a thickness of about 0.05 to about 2.0 mm. Optionally, the biocompatible polymer sheet can have a thickness of about 0.25 to about 1.2 mm or about 0.5 to about 1.0 mm. The length and width of the biocompatible polymer sheet should be sufficiently large to fit over the mold and include excess material for fixing the outer edges of the biocompatible polymer sheet to the frame. An exemplary biocompatible polymer sheet is Rapidsorb, a PLGA polymer sheet, available from DePuy Synthes CMF (West Chester, PA) in 8 mm and 1.2 mm thickness.

Figure 4A:
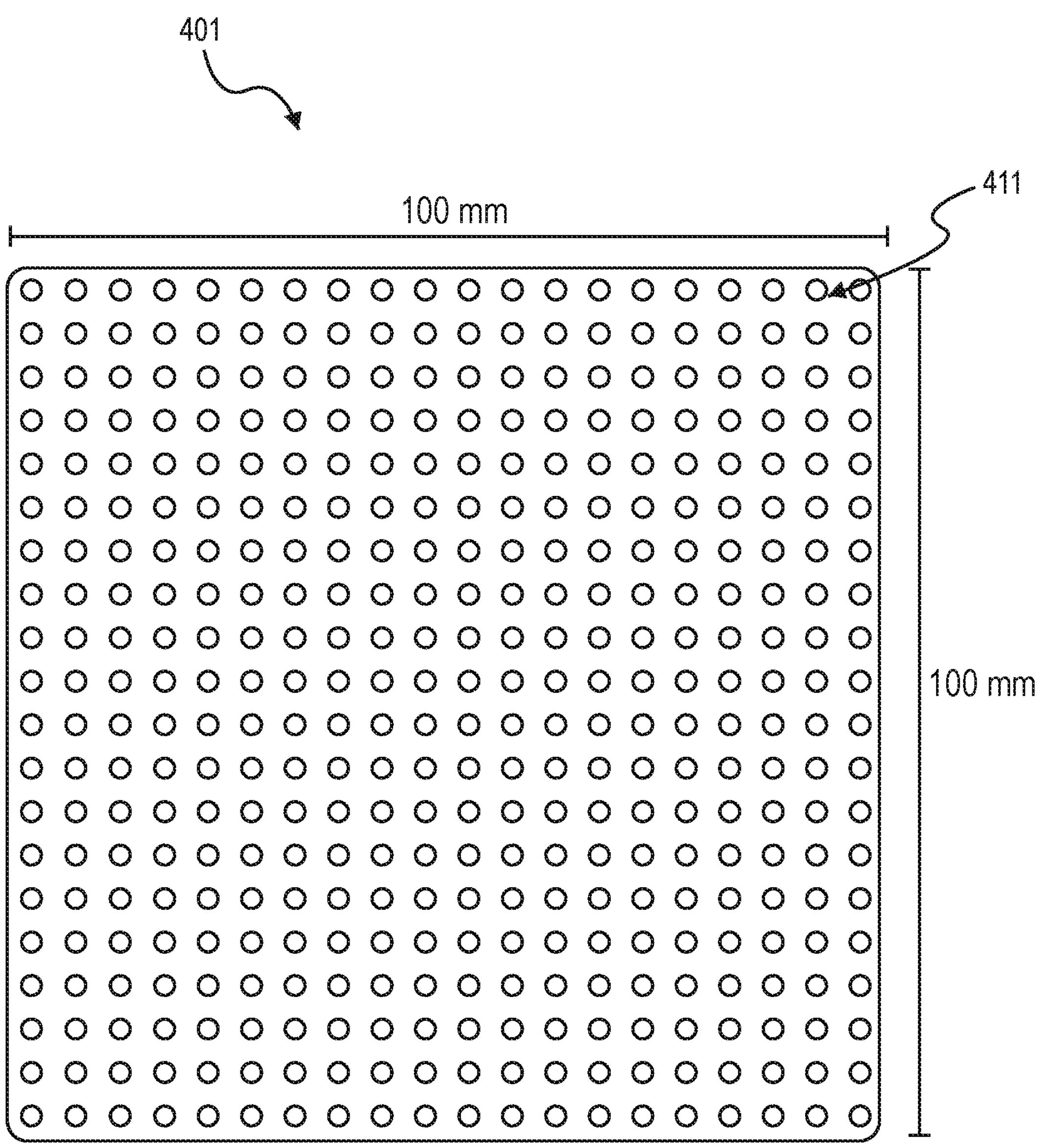
FIG. 4A depicts exemplary biocompatible polymer sheets including a plurality of holes that are round in shape and arranged in rows and columns in accordance with the present teachings.
Figure 4B:
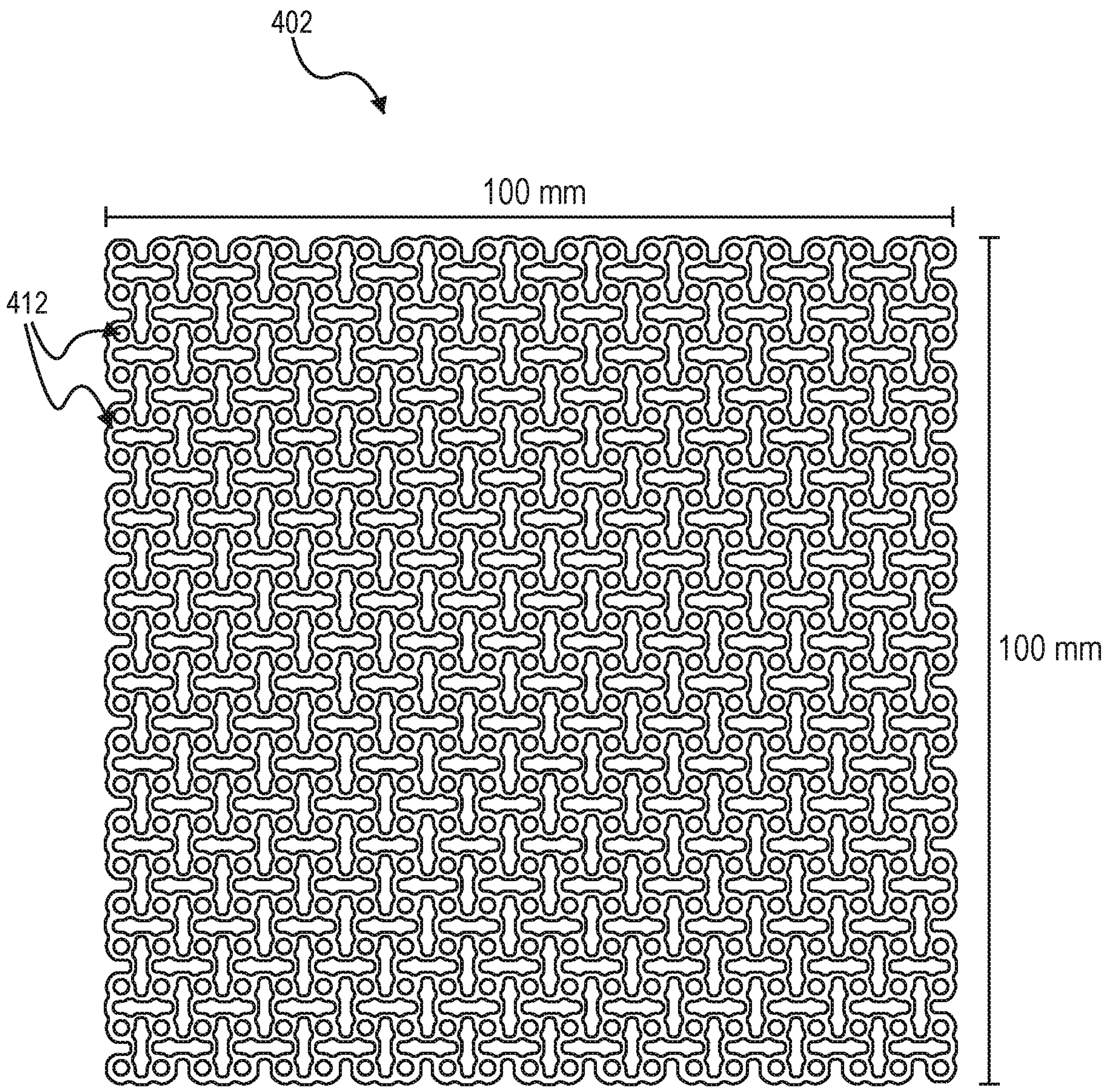
FIG. 4B depicts another exemplary biocompatible polymer sheets including a plurality of holes two different shapes in accordance with the present teachings.

Optionally, the biocompatible polymer sheet can include a plurality of holes that serve as pores in the completed auricular scaffold. The number and location of the holes can be random or be in a specific pattern to facilitate packing, retention, and/or structural stability when packed with crushed cartilage to form an auricular implant, also referred to herein as a neoauricular complex that can be implanted in a patient. For example, the holes can be about 0.5 to about 2.0 mm in diameter. The upper limit of the size and number of holes can depend on the power of the vacuum system used to form the scaffold. Examples of a biocompatible polymer sheet including a plurality of holes are shown in FIGS. 4A-B. FIG. 4A shows a biocompatible polymer sheet 401 having a thickness of 0.5 mm and a length of 100 mm and a width of 100 mm. Although depicted as round and arranged in straight rows and columns, plurality of holes 411 can have any desired shape and can be arranged in straight rows, diagonal rows, or as desired. FIG. 4B shows a biocompatible polymer sheet 402 having a thickness of 0.25 mm and a length of 100 mm and a width of 100 mm and having a variety of shaped holes 412.

The biocompatible polymer sheet should be uniformly heated to the first temperature. The first temperature depends on the type of biocompatible polymer sheet but should be sufficiently high to allow thermoforming. In other words, the first temperature should allow the biocompatible polymer sheet to be sufficiently pliable that when vacuum is drawn, the biocompatible polymer sheet moves downwardly onto the surface of the mold and conforms exactly to the mold surface taking on the shape of all the curves, crevices, and pores of the mold. For example, PLGA should be uniformly heated to a first temperature of about 65° C. to about 75° C.

At 130 of method 100, the biocompatible polymer sheet, heated to the first temperature, is placed in contact with the mold. As the biocompatible polymer sheet is drawn down over the mold, the biocompatible polymer sheet begins to take the shape of the mold.

At 140 of method 100, a vacuum is applied to the mold side of the biocompatible sheet to conform the biocompatible polymer sheet to the mold surface by a vacuum forming system known in the art. One of ordinary skill in the art can determine the amount of vacuum to apply based on a number of factors including, but not limited to, the type and thickness of the biocompatible polymer sheet and the vacuum forming equipment being used. Optionally, a positive pressure can further be applied to a side of the biocompatible polymer sheet opposite the mold to assist the biocompatible polymer sheet in taking on the shape of the mold.

After completion of forming the biocompatible polymer sheet to take on the shape of the mold, the biocompatible polymer sheet is cooled at 150 of method 100. Cooling to a temperature below the first temperature allows the shape of the mold to be fixed in the biocompatible polymer sheet.

At 160 of method 100, the cooled biocompatible polymer sheet having taken on the shape of the mold, can be removed from the mold and excess biocompatible polymer sheet can be trimmed away to form the auricular scaffold.

Figure 2:
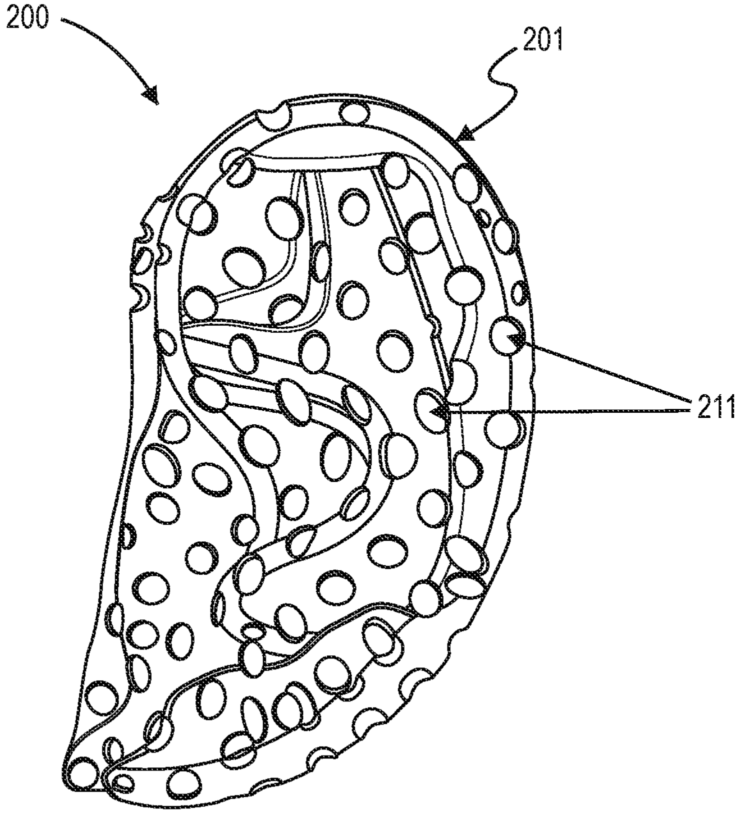
FIG. 2 depicts a polymer auricle scaffold formed by vacuum forming in accordance with the present teachings.

FIG. 2 shows a polymer auricular scaffold 200 formed by method 100 subsequent to removal from the mold. Polymer auricular scaffold 200 can be a single sheet of biocompatible polymer 201 vacuum formed using a mold to have a shape and a size representing an auricle. Single sheet of biocompatible polymer 201 forming polymer auricular scaffold 200 can be, for example, poly(lactic-co-glycolic acid) (PLGA) or poly (l-lactic acid) (PLLA) of varying levels of cross-linking and percentages of lactic and glycolic acid. The percentages of lactic acid to glycolic acid can vary, for example, from 85:15 to 75:25. Because polymer auricular scaffold 200 is formed by a single sheet of biocompatible polymer, no texturing or patterning from 3D printing are introduced. As used herein, the term "texture" refers to patterns in a 3D printed object resulting from the layer by layer deposition and/or variations in 3D printing apparatus including variations from a feeder, a positioner, or heating device. Examples of texture introduced by 3D printing includes, for example, banding texture on the surface of the 3D printed object due to a thickness of the printed layers or attachment texture near the 3D printed parts edge due to change in direction of the 3D printer. Methods for detecting and measuring texture from 3D printing are known to those of ordinary skill in the art. As a result, 3D printed auricular scaffolds have a surface roughness on the order of the thickness of each printed layer. In contrast, polymer auricular scaffold 200, formed from single sheet of biocompatible polymer 201, can have a surface roughness Ra of about 10 or less. Polymer auricular scaffold 200, formed from single sheet of biocompatible polymer 201, can optionally have a surface roughness Ra of about 5 or less or in some cases of about 3 or less. These levels of surface roughness are advantageously achieved without further processing subsequent to vacuum forming.

Polymer auricular scaffold 200 can include a plurality of holes 211 that extend fully or partially through the single sheet of biocompatible polymer. Plurality of holes 211 serve as pores that facilitate packing, retention, and/or structural stability of crushed cartilage packed within polymer auricular scaffold 200 to form an auricular implant . The number and location of the holes can be random or be in a specific pattern to facilitate packing, retention, and/or structural stability when packed with crushed cartilage. For example, the holes can be about 0.5 to about 2.0 mm in diameter and the upper limit of the size and number of holes can depend on the power of the vacuum system.

Figure 3:
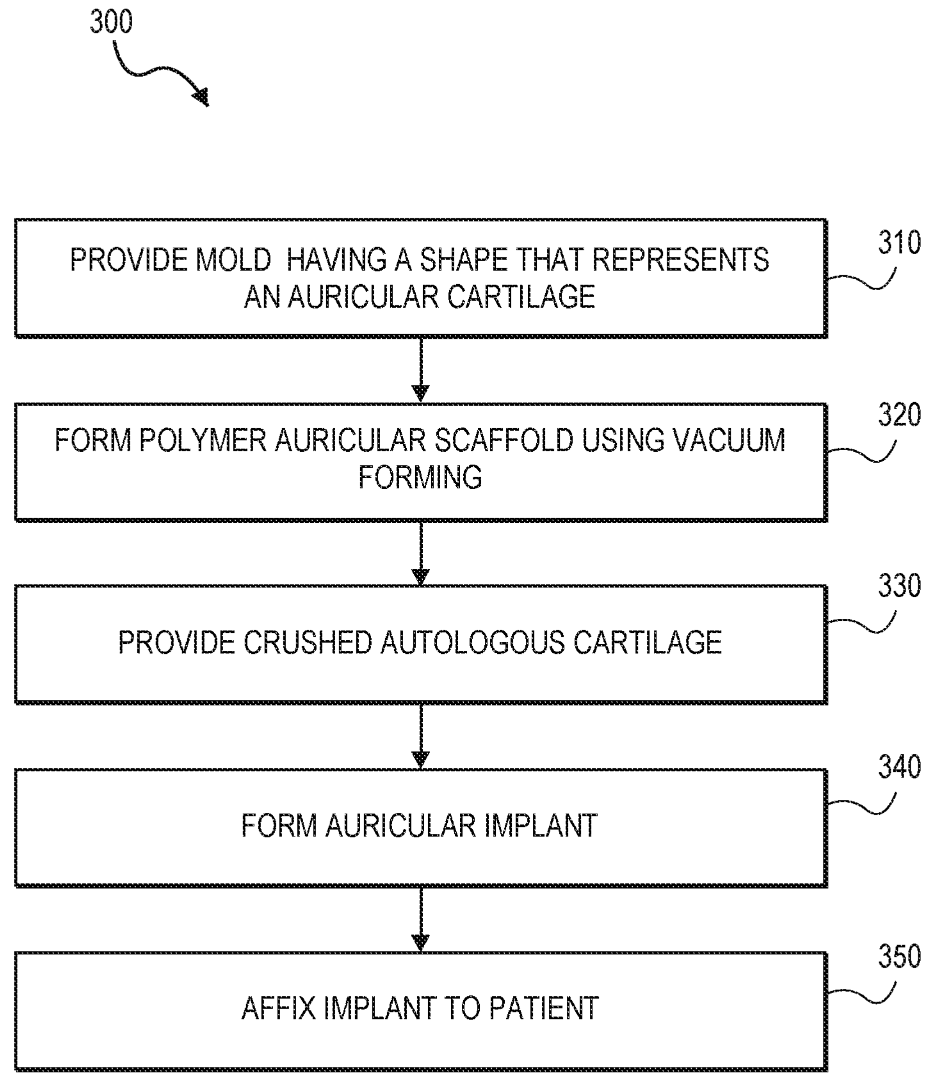
FIG. 3 depicts a method to reconstruct an auricle using an implant including a polymer auricle scaffold formed by vacuum forming in accordance with the present teachings.

FIG. 3 depicts a method 300 for reconstructing an auricle of a patient in accordance with the teachings of the present disclosure. At 310 of method 300, a mold is provided. The mold has a shape representing an auricle and can have a size and shape that varies dependent on the patient requiring the auricular graft. Standardized shapes and sizes can be used depending on the patient's age, sex, and size. Optionally, a customized mold can be fabricated by measuring the auricular cartilage of a patient, for example, using CT segmentation or 3D-profilometry. A data file can then be created based on the CT segmentation data or 3D-profilometry data. Using the data file, the customized mold can be 3D printed by methods disclosed herein.

At 320 of method 300, a polymer auricular scaffold is formed by vacuum forming. For example, the polymer auricular scaffold can be formed by method 100 disclosed herein.

At 330 of method 300, crushed autologous cartilage can be provided. Autologous cartilage, for example, costal cartilage obtained from the rib area, auricular cartilage harvested from the contralateral ear, or a combination of both. The crushed autologous cartilage can be mixed with either or both of tissue glue and platelet rich plasma. Exemplary tissue glue includes, but is not limited to, Evicel from J&J Medical Devices (New Brunswick, NJ) and Tisseel from Baxter (Deerfield, IL). The autologous cartilage can be crushed by hand or using a device to mechanically crush the cartilage.

At 340 of method 300, an auricular implant can be formed by packing the polymer auricular scaffold with the crushed autologous cartilage. For example, the crushed autologous cartilage mixed with tissue glue and/or platelet rich plasma can be packed into the auricular implant by hand.

At 350 of method 300, the auricular implant can be implanted in a patient using techniques known in the art.

Figure 5B:
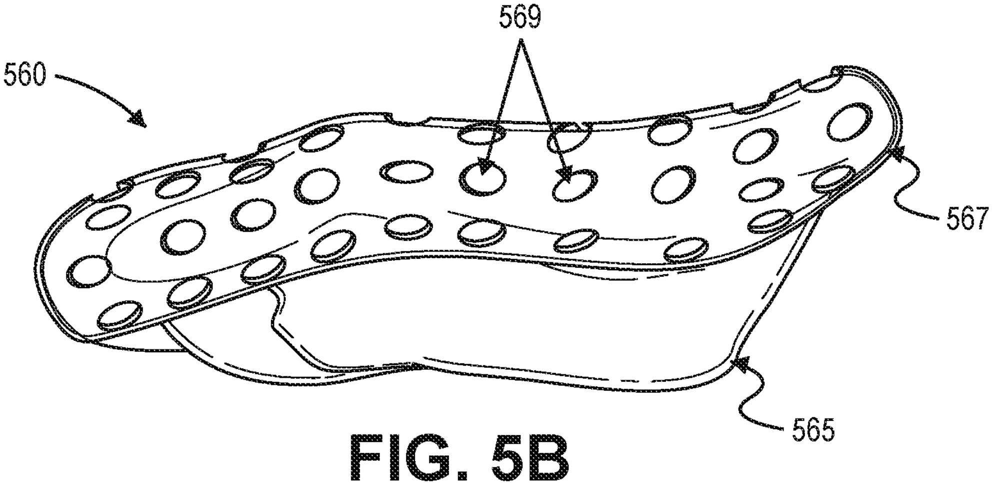
FIG. 5B depicts an auricular scaffold formed from a single sheet of biocompatible polymer mounted in a vacuum forming frame immediately after vacuum forming in accordance with the present teachings.
Figure 5A:
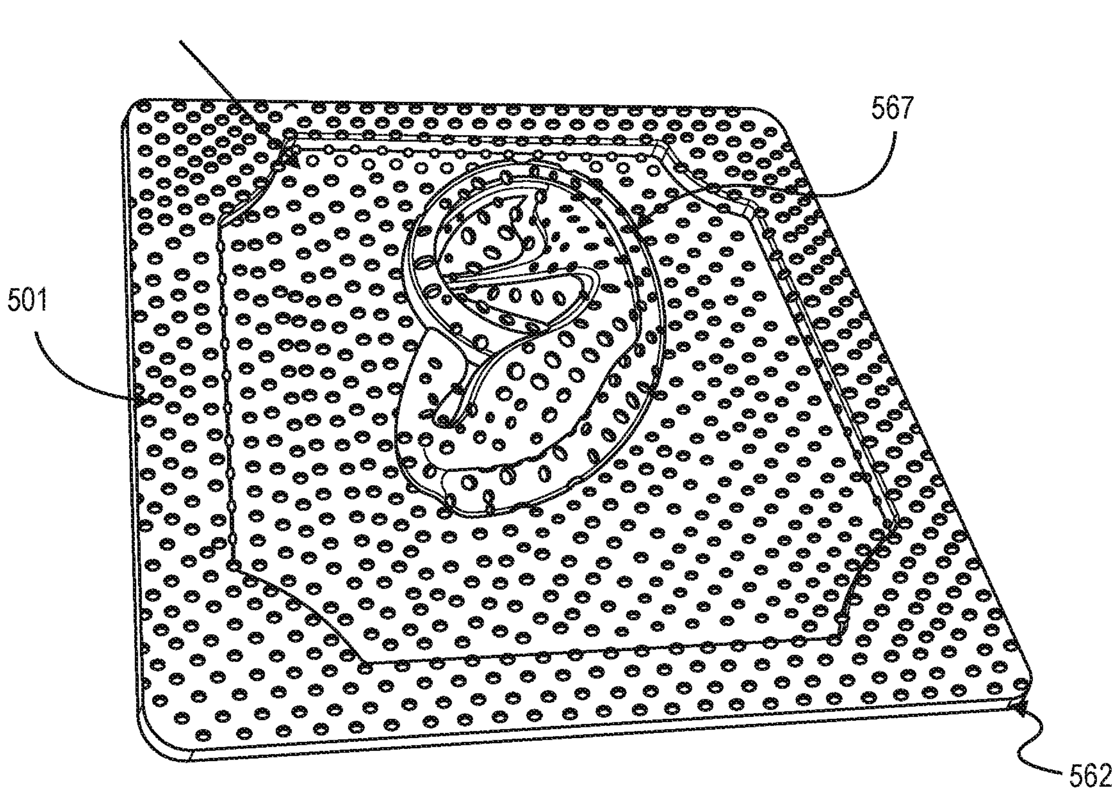
FIG. 5A depicts an auricular scaffold structure including a vacuum forming mold and an auricular scaffold disposed on the vacuum forming mold in accordance with the present teachings.

According to the present teachings an auricular scaffold structure 560 is also provided. FIGS. 5A-B show an auricular scaffold structure 560. FIG. 5A depicts auricular scaffold structure 560 including a vacuum forming mold 565 representing an auricular cartilage, for example of a patient. As discussed herein, vacuum forming mold 565 has a shape that represents an auricular cartilage and can have a size and shape that varies dependent on the patient requiring the auricular graft. For example, standardized shapes and sizes can be used depending on the patient's age, sex, and size. Optionally, a customized vacuum forming mold can be fabricated by measuring the auricular cartilage of a patient's contralateral ear of normal anatomy, for example, using CT segmentation or 3D-scanning. A data file can then be created based on the CT segmentation data or 3D-scanning data. Using the data file, the customized vacuum forming mold can be made, for example, by additive manufacturing.

Auricular scaffold structure 560 further includes an auricular scaffold 567 disposed on vacuum forming mold 565, wherein the auricular scaffold comprises a biocompatible polymer. As discussed herein, auricular scaffold 567 can be formed from a polymer sheet comprising a biocompatible polymer, including, but not limited to, poly(lactic-co-glycolic acid) (PLGA) and poly (I-lactic acid) (PLLA) of varying levels of cross-linking and percentages of lactic and glycolic acid. The biocompatible polymer sheet can have a thickness of about 0.05 to about 2.0 mm, about 0.25 to about 1.2 mm or about 0.5 to about 1.0 mm.

Auricular scaffold 567 can include a plurality of holes 569. The number and location of the holes can be random or be in a specific pattern to facilitate packing, retention, and/or structural stability when packed with crushed cartilage to form the auricular implant.

FIG. 5B depicts an auricular scaffold structure 567 immediately subsequent to vacuum forming. A single sheet of biocompatible polymer 501 can be mounted in a vacuum forming frame 562. Mounting single sheet of biocompatible polymer 501 on frame 562 facilitates heating and the subsequent steps of vacuum forming the biocompatible polymer sheet to take on the size and shape of mold 565. The length and width of the biocompatible polymer sheet 501 should be sufficiently large to fit over mold 565 and include excess material 569 for fixing the outer edges of the biocompatible polymer sheet to frame 562. Once a portion of single sheet of biocompatible polymer 501 has taken on a size and shape of mold 565 subsequent to vacuum forming, for example, at 320 of method 300 depicted in FIG. 3, auricular scaffold 567 is formed. After sufficient cooling, excess sheet of biocompatible polymer 501 can be removed by trimming excess material 503 to form auricular scaffold structure 560 including auricular scaffold 567 disposed on vacuum forming mold 565.

As further discussed herein, auricular scaffold 567 can have a surface roughness Ra of about 10 or less. Auricular scaffold 567, formed from single sheet of biocompatible polymer 501, can optionally have a surface roughness Ra of about 5 or less or in some cases of about 3 or less achieved without further processing subsequent to vacuum forming. Further, auricular scaffold 567 being vacuum formed from single sheet of biocompatible polymer 501 includes no texturing or patterning introduced by 3D printing.

While the present teachings have been illustrated with respect to one or more implementations, alterations and/or modifications can be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. For example, steps of the methods have been described as first, second, third, etc. As used herein, these terms refer only to relative order with respect to each other, e.g., first occurs before second. Also, not all process stages may be required to implement a methodology in accordance with one or more aspects or implementations of the present teachings. It will be appreciated that structural components and/or processing stages can be added or existing structural components and/or processing stages can be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. As used herein, the term "one or more of" with respect to a listing of items such as, for example, A and B, means A alone, B alone, or A and B. The term "at least one of" is used to mean one or more of the listed items can be selected. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "about" indicates that the value listed may be somewhat altered, as long as the alteration does not result in nonconformance of the process or structure to the illustrated implementation. Finally, "exemplary" indicates the description is used as an example, rather than implying that it is an ideal. Other implementations of the present teachings will be apparent to those skilled in the art from consideration of the specification and practice of the disclosure herein. It is intended that the specification and examples be considered as exemplary only, with a true scope and spirit of the present teachings being indicated by the following claims.

What is claimed is:

1. A method of forming an auricular scaffold comprising:

providing a mold comprising a shape and a size representing an auricular cartilage;

heating a biocompatible polymer sheet to a first temperature, wherein the biocompatible polymer sheet comprises a plurality of holes from about 0.5 mm to about 2.0 mm in diameter prior to heating, and wherein the holes extend through the biocompatible polymer sheet;

contacting the biocompatible polymer sheet that was heated to the mold;

applying a vacuum to the biocompatible polymer sheet that was heated to draw the biocompatible polymer sheet over the mold;

cooling the biocompatible polymer sheet, that was drawn over the mold, below the first temperature to fix the shape representing the auricular cartilage in the biocompatible polymer sheet, removing the biocompatible polymer sheet that was drawn over the mold and cooled from the mold; and trimming excess biocompatible polymer sheet to form the auricular scaffold, wherein the plurality of holes are positioned to facilitate one or more of packing, retention, and structural stability of crushed cartilage packed within the auricular scaffold.

2. The method of claim 1, wherein providing a mold comprises:

creating a data file representing the auricular cartilage of a patient; and printing, by additive manufacturing, the mold using the data file.

3. The method of claim 2, wherein the data file represents measurements made by CT segmentation or three dimensional (3D)-scanning.

4. The method of claim 2, wherein printing by additive maufacturing is by one or more of stereolithography (SLS), fused deposition modeling (FDM), selective laser sintering (SLS), fused deposition modeling (FDM), digital light processing (DLP), selective laser melting (SLM), laminated object manufacturing (LOM), and electron beam melting (EBM).

5. The method of claim 1, wherein the biocompatible polymer sheet comprises one or more of poly (lactic-co-glycolic acid) (PLGA), poly (1-lactic acid) (PLLA), or other biocompatible polymers.

6. The method of claim 1, wherein the biocompatible polymer sheet has a thickness of about 0.05 mm to about 2 mm.

* * * * *